United States Patent [19]

Leveen et al.

[11] Patent Number: 5,070,889
[45] Date of Patent: Dec. 10, 1991

[54] CONTRACEPTIVE SPONGE AND TAMPON

[76] Inventors: Harry H. Leveen, 321 Confederate Cir., Charleston, S.C. 29407; Robert F. Leveen, 312 Lombard St., Philadelphia, Pa. 19147; Eric G. Leveen, 19 Palmetto Rd., Charleston, S.C. 29407

[21] Appl. No.: 614,089

[22] Filed: Nov. 15, 1990

Related U.S. Application Data

[63] Continuation-in-part of Ser. No. 318,178, Mar. 2, 1989, Pat. No. 5,000,749, which is a continuation-in-part of Ser. No. 257,062, Oct. 13, 1988, Pat. No. 4,968,439.

[51] Int. Cl.$^5$ .............................................. A61F 6/06
[52] U.S. Cl. ..................................... 128/830; 128/832
[58] Field of Search ................. 128/830, 841; 604/11, 604/55, 358, 359, 360, 904; 424/431

[56] References Cited

U.S. PATENT DOCUMENTS

| 4,309,997 | 1/1982 | Donald | 604/11 |
| 4,393,871 | 7/1983 | Vorhauer | 604/58 |
| 4,661,101 | 4/1987 | Sustmann | 604/360 |
| 4,784,989 | 11/1988 | Höök | 514/21 |

Primary Examiner—Robert A. Hafer
Assistant Examiner—Michael Brown
Attorney, Agent, or Firm—John S. Hale

[57] ABSTRACT

A bacteriocidal virocidal sponge containing iodine and/or chlorhexidine and a surfactant which can be used as a contraceptive and virocidal and bacteriocidal sponge positioned within a human body comprising a polyurethane open cell foam impregnated with a surfactant and iodine and/or chlorhexidine. A bactericidal tampon containing an iodophor or chlorhexidine does not induce toxic shock syndrome.

9 Claims, 2 Drawing Sheets

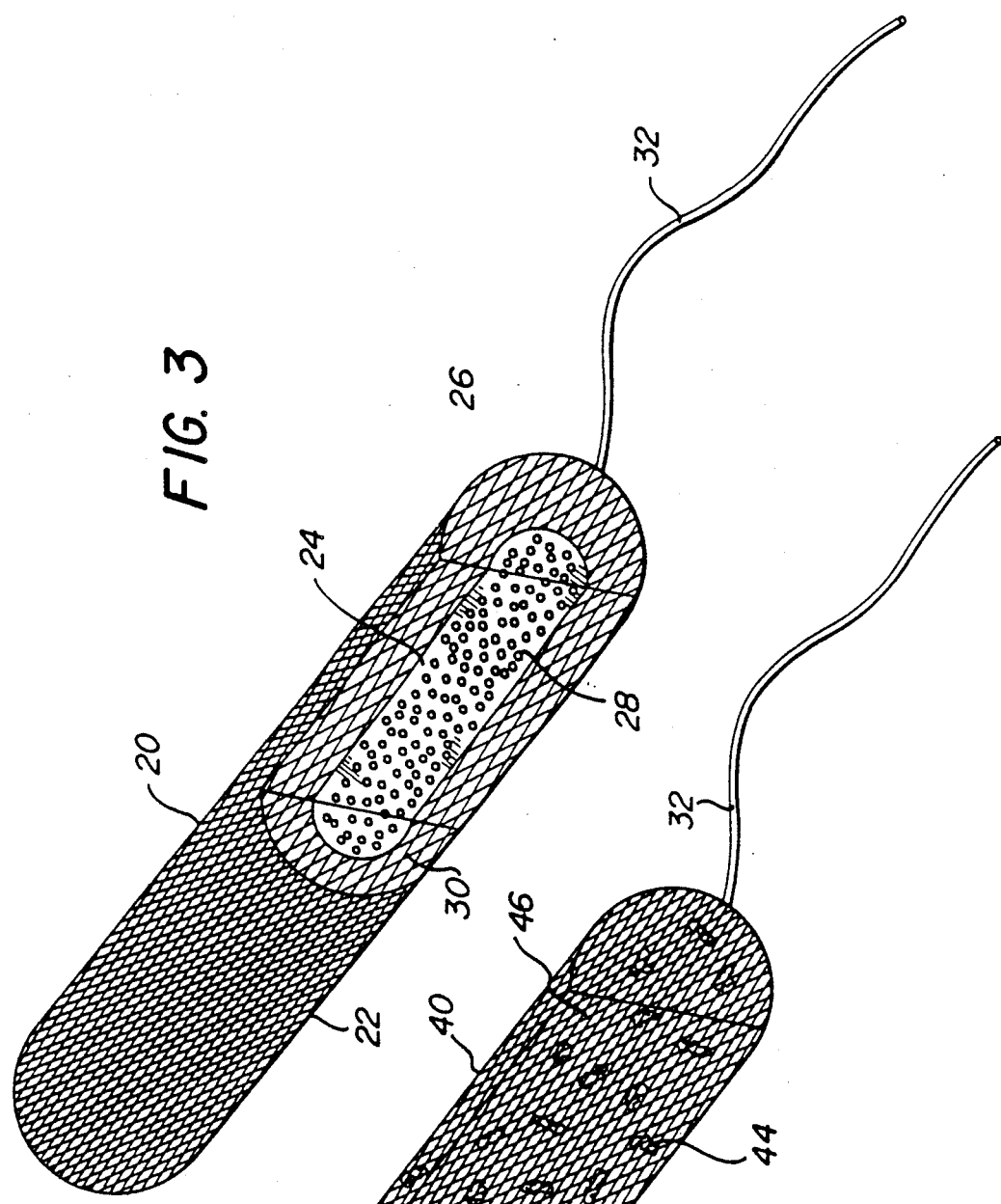

CONTRACEPTIVE SPONGE AND TAMPON

RELATED APPLICATIONS

This is a continuation-in-part application of U.S. patent application Ser. No. 318,178 filed Mar. 2, 1989, now U.S. Pat. No. 5,000,749, which is a continuation-in-part application of U.S. patent application Ser. No. 257,062 filed Oct. 13, 1988, now U. S. Pat. No. 4,968,439.

BACKGROUND OF THE INVENTION

In recent years there has been a serious increase in sexually transmitted disease. Sexual freedom among consenting adults has been a partial cause of this increase. In addition, oral contraceptives and a change in the mores has created a situation which has increased the number of sexual contacts, thus favoring dissemination of sexually transmitted disease. Since these factors are unlikely to change, sexually transmitted disease has now become a major public health problem. Some diseases which were formerly unassociated with sexual transmission, such as B virus hepatitis, are now known to be sexually transmitted. Other new diseases such as acquired immune deficiency syndrome (AIDS) are viral diseases which are usually transmitted sexually. A need therefore exists for all conceivable types of control measures to reverse the increasing incidence of sexually transmitted disease.

The intravaginal contraceptive doughnut shaped sponge containing a spermicidal agent has become an accepted method of birth control in western society. Yet this sponge does little to halt the incidence of sexually transmitted disease which is steadily increasing. Such sponges are formed of an open cell polyurethane foam sponge impregnated with a spermicidal agent, nonoxynol-9, (U.S. Pat. No. 2,541,103). Nonoxynol is a polyethylene glycol nonylphenyl ether which is a mild surfactant. Like other non ionic surfactants it is a cytolytic agent which acts by disrupting the plasma membrane of animal cells. It is not as effective on the cell walls of bacteria which are unlike the lipid containing membranes of animal cells. Unfortunately, nonylphenoxypolyethoxyethanol is only bacteriostatic and not bacteriocidal when placed in a culture of staphlococcus aureus (TSS-S aureus). Toxic shock syndrome (TSS) is caused by the proliferation of staphlococcus aureus in absorbent tampons at the time of menstruation and in contraceptive sponges used in the absence of menstruation. Although nonoxynol does suppress colony counts of staphlococcus aureus during the first 6 hours of growth in a culture medium, the number of bacteria in the culture flask after 30 hours has been shown to be identical to that of control cultures. (Contraception 33:395 1986). Therefore, nonoxynol does not prevent the growth of staphlococci in contraceptive sponges and the absorption of the toxins from proliferating staphlococci can produce toxic shock syndrome. Thirteen cases have been reported in users of a contraceptive sponge impregnated with nonoxynol. (Int Fertil [Sweden] 30:81 1985). In all of these cases, TSS-S aureus was cultured. It has been estimated that the incidence of TSS would be 10 cases a year per 100,000 women using the sponge. To prevent TSS, contraceptive sponges must contain a bacteriocidal agent in addition to nonoxynol. The current mortality from TSS is 3% (J.A.M.A. 251:1016 1984). The death rate in contraceptive sponge users is less than that occurring with tampons where the incidence of TSS is also 10 per 100,000 menstrual users (NEJM 303:1429 1980). Even though nonoxynol is only bacteriostatic, a study of prostitutes in Bangkok, Thailand who used nonoxynol-9 intravaginal contraceptive sponges showed that these prostitutes had a lower incidence of venereal disease (chlamydial infection and gonorrhea) than those who did not use this contraceptive sponge. (J.A.M.A. 257:2308 1987). The incidence of monilia vaginitis was increased because nonoxinol is not fungicidal. The slight reduction in the incidence of venereal disease in frequently exposed prostitutes is not acceptable with regard to disease prevention and the decrease in incidence is eventually eliminated by frequency of exposure. If a contraceptive sponge could be made which contained virocidal, bactericidal and fungicidal agents in addition to the spermicide, it would completely protect against sexually transmitted disease. Such a sponge would not only protect the female from sexually transmitted disease, but would be equally protective for the male. This consideration has not been addressed by the medical literature. Bactericidal tampons would eliminate the possibility of toxic shock syndrome. Such developments would fulfill major public health needs and lead to a reduction in the rate of sexually transmitted disease.

SUMMARY OF THE INVENTION

The present invention describes a bacteriocidal, virocidal and protozocical contraceptive sponge which, unlike a sponge which relies totally on a spermicidal agent which cannot prevent sexually transmitted disease, liberates a biocidal agent. The present invention preferentially liberates iodine which is useful in treating vaginal infections (vaginitis) caused by trichomonas, gonococcus, monilia and chlamydia. A vaginal absorbent tampon which cannot induce toxic shock syndrome is also described. Furthermore, such a contraceptive sponge releasing iodine in addition to nonoxynol would lower the incidence of carcinoma of the cervix which is now known to be a manifestation of the sexually transmitted papilloma virus. Iodine would also prevent the transmission of the highly prevalent genital herpes which is known to predispose to malignancy.

Free iodine is the preferential bacteriocidal substance because it is non-toxic in low concentrations, there is no bacterial resistance to iodine and all organisms are susceptible. Nonetheless, other substances may be used to render tampons bacteriocidal. One such substance is chlorhexidine gluconate. Chlorhexidine gluconate is very effective against gram positive organisms in concentrations of 10 micrograms per milliliter and fungi at 200 micrograms per milliliter. The effectiveness of chlorhexidine gluconate is not significantly reduced by the presence of blood. Chlorhexidine gluconate is repidly acting and has low potential for producing contact sensitivity with long term clinical use. One of its major advantages is that it is poorly absorbed, lessening the chance of systemic toxicity. Chlorhexidine gluconate is relatively non-toxic and has even been approved by the FDA as a preservative for opthalmic preparations. Chlorhexidine gluconate is the only other suitable germicidal agent which may be used. Compounds such as gramicidin are extremely hemolytic and rapidly absorbed. They should not be used in situations where absorption is possible. The quaternary ammonia compounds such as benzalkonium chloride do not have a suitable germicidal spectrum, are systemically toxic and are inactivated by blood and proteins. Mercurial and other heavy metal compounds are only bacteriostatic and are systemically toxic. The present invention discloses a sponge which liberates small amounts of iodine and a spermicide from a polyurethane iodine complex. The iodine concentration is thereby established in the vagina to render it bacteriocidal, spermicidal, viricidal and protozoacidal without being irritative. The contraceptive sponge can also be used as a therapy for various types of infectious vaginitis. The contraceptive sponge of the present invention will not produce toxic shock syndrome and tampons manufactured with fragments of sponges containing iodine polyurethane complex can be used as a tampon for women during menses.

The present invention also discloses a tampon which liberates either iodine or chlorhexidine sufficiently to render it bacteriocidal and unable to produce toxic shock syndrome.

BRIEF DESCRIPTION OF THE DRAWINGS

FIG. 3 is a tampon using the sponge invention partially cut away to show a section of the interior; and FIG. 4 is another embodiment of the tampon invention partially cut away to show a section of the interior.

DETAILED DESCRIPTION OF THE INVENTION

Figure 1:
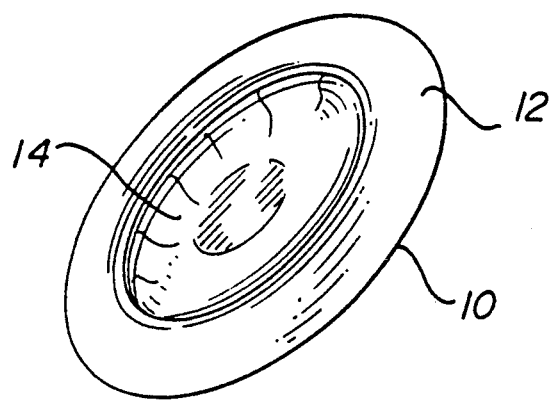
FIG. 1 is a perspective view of the contraceptive sponge invention.

The best mode and preferred embodiment of the invention is shown in FIG. 1. Iodine in concentration of 2+ parts per million is a strong disinfectant. Such concentrations of iodine are known to be germicidal, algaecidal, sporocidal, amoebacidal, mycocidal and viricidal. Chlorhexidine in concentrations of 10 micrograms per cubic centimeter is known to be bacteriocidal, and fungicidal in concentrations of 200 micrograms per cubic centimeter. The reduction of venereal disease by those who use a simple contraceptive sponge indicates that if the intravaginal contraceptive sponge were also spermicidal, bacteriocidal and virocidal, it would be a very efficient contraceptive and in addition it would protect against sexually transmitted disease and Toxic Shock Syndrome.

$I_2$ bonds to PVP between the carbonyl group and the nitrogen. $I_2$ complexes with polyurethane and releases the $I_2$ in a manner similar to that claimed for polyvinyl-pyrrolidone-iodine complex (PVP) (U.S. Pat. No. 4,381,380). Solid polyurethane-$I_2$ sponge has a large surface area whether made by foaming thermoplastic polyurethane with a blowing agent or making the sponge with a blowing agent as a thermoset. HYPOL TM polyurethane resin manufactured by W. R. Grace makes a satisfactory sponge merely by adding water. The latter method is usually employed in making polyurethane foam and because of its large surface area can bind considerable quantities of iodine and hold large amounts of chlorhexidine. Iodine has been found to possess superior germicidal properties. Chlorhexidine has also been found to possess strong bacteriocidal properties for gram positive bacteria. A polyurethane sponge by virtue of the great magnitude of surface area can bind large quantities of free iodine and contain suitable concentrations of chlorhexidine and is thus capable of liberating either of these substances continuously for many hours or days thus adding considerably to its therapeutic value.

Figure 2:
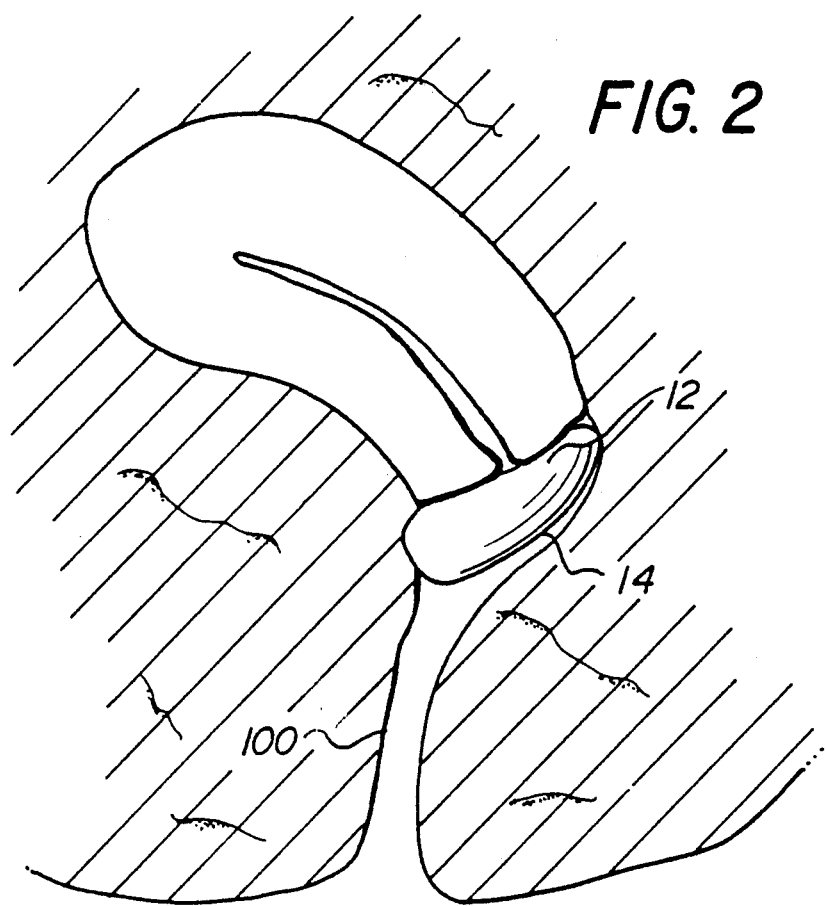
FIG. 2 is a partial cross section view of the sponge invention of FIG. 1 inserted into a cervical canal.

In the present invention a polyurethane contraceptive sponge 10 shaped like a shallow hat with a rim 12 and hollowed out concave central portion 14 is shown in FIG. 1. The sponge 10 forms a suitable barrier to the entrance of sperm into the cervical canal. Such a sponge is inserted into the vagina 100 in a folded position with the hollowed out concave portion 14 folded in and the edges on rim 12 pointing upward. After insertion the hollow area accommodates the cervix of the uterus as is shown in FIG. 2.

Iodine is complexed to polyurethane sponge 10 by the addition of free iodine in an aqueous solution of potassium iodide. Lugol's solution which is 5% $I_2$ dissolved in 10% sodium iodide solution can be used to complex the iodine with polyurethane. The sponge can be immersed in the Lugol's solution or the solution can be added drop wise to the sponge. The sponge is then washed with 0.2% sodium iodide solution to remove excess iodine and subsequently washed thoroughly with deionized water. Alternative methods are available to complex the sponge with iodine. The iodine can be dissolved in alcohol containing nonoxynol and allowed to dry depositing 20 to 40 mg of iodine for each gram of nonoxynol deposited. Alternatively, the iodine can be added to the nonoxynol prior to its addition to the sponge so that each sponge contains about 1 gram nonoxynol and 20 to 40 mg. iodine. Iodine is dissolved by surfactants such as nonoxynol which are themselves iodophors. Since iodine is more effective in acid solution, 5-20 milligrams of polyacrylic acid (Carbopol made by Goodrich) is added to keep the vaginal secretions acid.

The sponges can be obtained from any number of manufacturers but the open cell foam formed from W. R. Grace HYPOL TM resin has been used for contraceptive sponges. The sponges should be flexible and therefore polyether polyurethane rather than polyester. Polyether polyurethanes are more suitable although both function satisfactorily as iodine binders and an admixture of both may be necessary to arrive at a satisfactory durometer. The sponge should have very small open cells and as high a density as is compatible with maximum porosity. This exposes a maximum number of urethane linkages on the surface of the polyurethane where the complexing with the iodine takes place.

Aqueous saline solution with 2-4 ppm of $I_2$ is not inflammatory when instilled into the human eye and can be used to irrigate human tissue to prevent infection or to treat infected peritonitis (Stephen R. L. et al Dialysis & Transplantation page 662 June 1979). Aqueous Iodine Solution U.S.P. which contains 2% iodine in 2.4% sodium iodide is mentioned in A.M.A. Drug Evaluations 5th Ed. 1983 page 1385 as "preferred for superficial lacerations to prevent micobial infections, since it is effective and nonirritating." $I_2$ is an excellent broad spectrum non selective biocidal agent to which organisms do not develop resistance. $I_2$ has been locally used to treat bacterial and mycotic infections including bacterial skin infections, sore throats and mycotic infections of the toes, hands, ears, or perineal region. (J. Internat. Col. Surg. 25:727 1956) with clearing in 36 hours. Iodine has been successfully used to control infection on burns and traumatic skin loss (Brit. J. Plastic Surg 28:146 1965). Its use to sterilize the skin prior to surgical operations is well known although the use of the tincture has largely been replaced with iodophors, such as polyvinylpyrrolidone-iodine complex.

In many studies, iodine applied as a polyvinylpyrrolidone-iodine complex (povidone iodine) from which free iodine is supposedly liberated (U.S. Pat. No. 2,739,922). Iodophors have been found to be effective in treating resistance vaginitis (Current Ther. Res. 5:256, 1963). Iodine is effective against monilia (Plastic & Reconstruct. Surg. 29:648, 1962) and trichomonas (J. Newark Beth. Hosp. 6:129, 1955) as well as bacterial infections. Although iodine is presumed to dissociate from povidone-iodine, it has not been demonstrated that free iodine is liberated from povidone-iodine. Tampons impregnated with PVP-iodine have been used in most studies on vaginitis. PVP-iodine has the disadvantage of being a brown liquid which is absorbed from the vagina (JAMA 244:2628, 1980). It is toxic when it gains access to the circulation by absorption and causes death (Ann. Thor. Surg. 39:478, 1985; Ann. Thor. Surg. 43:239, 1987; West J. Med. 146:43, 1987). Povidone-iodine i not metabolized in the body. The PVP is ingested by phagocytes and giant cells where it remains for life, causing PVP storage disease, a granulomatous lesion (Pathology 20:83, 1988). Iodine-polyurethane complex is a solid iodophor and cannot be absorbed. It liberates free iodine which is in equilibrium with the polyurethane-iodine complex. This equilibrium can be set to liberate free iodine to form concentrations in an aqueous solution from 2 to 10 parts per million. Thus, the solid polyurethane-iodine complex which releases its free iodine (U.S. Pat. No. 4,381,380) is more effective and safer than the widely used povidone-iodine solutions.

EXAMPLES

Iodine sponges are effective in the treatment of senile vaginitis. In this disease, the absence of estrogens causes the failure of glycogen to appear in the vaginal mucosa. The vaginal secretions are kept acid by Doderlin bacteria normally present in the vagina which convert the glycogen to lactic acid. This neutralizes and makes non toxic the ammonia which would otherwise form in the vagina and irritate and inflame the vaginal mucosa. The iodine kills the urease producing bacteria and thus interrupts the production of ammonia. Polyacrylic acid restores the acidity of the vaginal secretions. The polyurethane-iodine sponge is curative for senile vaginitis. The polyurethane-iodine sponge is also curative for vaginitis caused by trichomonas, monilia, herpes, gonorrhea and other infective types of vaginitis. In such cases a new sponge is introduced once or twice a day for 5 days. Cultures or smears have confirmed the disappearance of monilia and trichomonas.

Another use of the iodine sponge is in absorbent tampons which are used by many females at the time of menses. All of these tampons are barriers which impede the discharge of shed blood and tissue and prolong its retention in the vagina. When those protein soaked tampons become contaminated with staphlococcus aureus, bacterial growth in the tampon can result in a high concentration of toxic bacterial products within the tampon. Absorption of these staplococcal toxins causes toxic shock syndrome characterized by fever, hypotension, nausea, lethargy, diffuse rash, desquamation, and a vaginal discharge. Vaginal cultures are positive for staphlococcus aureus. A mortality rate of 3% attests to the seriousness of the disease. The occurrence of toxic shock syndrome could be eliminated by making the tampons bacteriocidal. This can be done by incorporating polyurethane iodine sponge as a central core of the tampon or as small pieces of shredded iodine polyurethane-iodine complex so as to store at least 40 mg of releasable iodine in the tampon.

FIG. 3 shows an absorbent tampon 20 with a gauze covering 22. The core member 24 of the tampon 20 is a polyurethane sponge 26 which has been complexed with at least 20 mg of releasable iodine or chlorhexidine and contains air bubbles 28. Surrounding the core member 24 are absorbent cellulose fibers 30 which are covered by a wrapping of cotton gauze 22. A string 32 is attached to the gauze to permit withdrawal of the tampon.

An alternate tampon embodiment is shown in FIG. 4. The tampon 40 has an absorbent cellulose body 42 containing bits of polyurethane foam 44 which has been shredded and treated with iodine and/or chlorhexidine in the amount previously stated. The foam bits 44 are interplaced in absorbent cellulose 46. The tampon is wrapped with gauze (not shown) identical to the tampon of FIG. 3 and is provided with a similar string.

The polyurethane tampon material may contain dry chlorhexidine gluconate in place of iodine so that the concentrations when moist contain about 25 to 100 micrograms of chlorhexidine per ml of blood. This usually requires a total amount of chlorhexidine gluconate of 5 to 10 milligrams per tampon and 2.5 milligrams for a contraceptive sponge. The chlorhexidine gluconate may be applied to the polyurethane sponge in an alcohol solution allowing the alcohol to evaporate to leave a solid residue of chlorhexidine.

In the foregoing description, the invention has been described with reference to a particular preferred embodiment, although it is to be understood that specific details shown are merely illustrative, and the invention may be carried out in other ways without departing from the true spirit and scope of the following claims:

What is claimed:

1. A bacteriocidal virocidal sponge member for insertion into the vagina in the form of an open cell foam impregnated with an iodine and chlorhexidine polyurethane complex, said sponge member being hat shaped and said open cell foam is treated with iodine to continuously liberate iodine into the human body said foam having in a concentration of iodine ranging from 1 to 5 parts per million.

2. A sponge member as claimed in claim 1 wherein said sponge comprises a circular rim with a concave interior portion.

3. A sponge member as claimed in claim 1 wherein said open cell foam is treated with a solution of elemental iodine dissolved in a non ionic surfactant.

4. A sponge member as claimed in claim 3 wherein said surfactant includes an acid solution for the purpose of keeping vaginal secretions acid.

5. A sponge member as claimed in claim 4 wherein said acid solution is polyacrylic acid and the amount added ranges from 5 to 20 milligrams.

6. A sponge member as claimed in claim 1 wherein said open cell foam has small open cells of high density and a chlorhexidine concentration of about 2.5 milligrams.

7. A sponge member as claimed in claim 1 wherein said open cell foam is of the polyether variety.

8. A sponge member as claimed in claim 7 wherein said polyether variety is a polyether polyurethane.

9. A sponge member as claimed in claim 1 wherein said open cell foam is impregnated only with chlorhexidine polyurethane.

* * * * *